United States Patent [19]

Baumeister et al.

[11] Patent Number: 4,960,936

[45] Date of Patent: Oct. 2, 1990

[54] PROCESS FOR THE PREPARATION OF HALOGENATED AROMATIC PRIMARY AMINES

[75] Inventors: Peter Baumeister, Flüh; Wilfried Scherrer, Bubendorf, both of Switzerland

[73] Assignee: Ciba-Geigy Corporation, Ardsley, N.Y.

[21] Appl. No.: 286,102

[22] Filed: Dec. 19, 1988

[30] Foreign Application Priority Data

Dec. 31, 1987 [CH] Switzerland ............... 5126/87

[51] Int. Cl.$^5$ .................................. C07C 209/36
[52] U.S. Cl. ................................ 564/417; 564/415; 564/416
[58] Field of Search ............................. 564/417

[56] References Cited

U.S. PATENT DOCUMENTS

| 3,361,819 | 1/1968 | Kosak et al. | 564/417 |
| 3,989,756 | 11/1976 | Fujise et al. | 564/417 |
| 4,059,627 | 11/1977 | Kritzler et al. | 564/417 |
| 4,070,401 | 1/1978 | Hirai et al. | 564/417 |
| 4,267,324 | 5/1981 | Sparks et al. | 544/262 |
| 4,375,550 | 3/1983 | Bird et al. | 564/417 |

FOREIGN PATENT DOCUMENTS

| 2441650 | 3/1975 | Fed. Rep. of Germany | 564/417 |
| 1191610 | 5/1970 | United Kingdom | 564/417 |

OTHER PUBLICATIONS

Grant & Hackh's Chemical Dictionary, Fifth Edition, p. 243, "Formamidine", 1987.
Trumpler et al., Helv. Chim. Acta. vol. 39, pp. 407–416 (1959).

Primary Examiner—Glennon H. Hollrah
Assistant Examiner—S. J. Treanor
Attorney, Agent, or Firm—Michael W. Glynn

[57] ABSTRACT

The catalytic hydrogenation of halogenated nitro aromatics using Raney nickel in the presence of a formamidine salt as dehalogenation inhibitor affords halogenated aromatic primary amines in high yields and high chemical purity within short reaction times even at elevated temperatures.

20 Claims, No Drawings

PROCESS FOR THE PREPARATION OF HALOGENATED AROMATIC PRIMARY AMINES

The invention relates to a process for the preparation of halogenated aromatic primary amines by catalytic hydrogenation of halogenated aromatic nitro compounds in the presence of Raney nickel and a formamidine salt as dehalogenation inhibitor.

It is known that halogenated aromatic primary amines are obtained by catalytic hydrogenation of halogenated aromatic nitro compounds. The hydrogenation additionally leads to a dehalogenation and thus to mixtures of halogen-free and halogenated aromatic primary amines which are difficult to separate.

DE-AS No. 2,441,650 describes a hydrogenation process in the presence of Raney nickel in which dicyanodiamide, cyanamide or calcium cyanamide is used as dehalogenation inhibitor. It is also disclosed that the dicyanodiamide is partially hydrogenated. However, since the reaction mixture is basic, no formamidine salt can be formed as a stable intermediate. The reason is that, as G. Trumpler et al. already described in Helv. Chim. Acta, 39, p. 407–416 (1959), in the catalytic hydrogenation of cyanamide using Raney nickel, formamidine salts are only formed as primary reaction products under weakly acidic conditions (pH≈6).

It has now been found that formamidine salts suppress dehalogenation during the hydrogenation of halogenated aromatic nitro compounds even at elevated temperatures in an efficient manner. The desired halogenated aromatic amines are obtained in higher, under favourable conditions in virtually quantitative, yields compared to those obtained in the reaction without additives, and the percentage of byproducts can be substantially below 1% by weight under optimum conditions. The catalyst activity is not impaired so that the Raney nickel can be used repeatedly. The hydrogenation rate is not affected significantly. The process is suitable for being carried out on an industrial scale.

The invention relates to a process for the preparation of halogenated aromatic primary amines by catalytic hydrogenation of halogenated aromatic nitro compounds in the presence of Raney nickel at a pressure of 0.1 to 100 bar and at a temperature of 30° to 150° C. in an inert solvent and in the presence of an inhibitor against dehalogenation, wherein the inhibitor is a formamidine salt.

Examples of suitable nitro compounds are those of the general formula

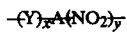

in which x and y, independently of one another, are a number from 1 to 6, preferably 1 to 3 and in particular 1 or 2, Y is halogen, in particular F, Cl and Br and A is an aromatic radical having 6 to 18 carbon atoms which can additionally contain further substituents. Y is in particular Cl or Br.

The aromatic radical preferably contains 6 to 14, in particular 6–10, carbon atoms and represents in particular an aromatic hydrocarbon radical. Examples of aromatic hydrocarbons from which the radical can be derived are, for example: benzene, naphthalene, phenanthrene, biphenyl, indane, benzene linked by bridging groups $Y^1$ stable to hydrogenation, for example

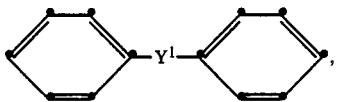

in which $Y^1$ can be $C_1$–$C_4$alkylene, $C_1$–$C_6$alkylidene, —O—, —S—, —SO$_2$— or —CO—.

Further examples of suitable substituents for the radical A are $C_1$–$C_4$alkyl, $C_1$–$C_4$halogenoalkyl, $C_1$–$C_4$alkoxy, $C_1$–$C_4$halogenoalkoxy or $C_1$–$C_4$alkylthio, $C_5$cycloalkyl or $C_6$cycloalkyl, cyano, hydroxyl, $C_1$–$C_8$acyl or $C_1$–$C_8$acyloxy, —COOH, —SO$_3$H, —COOM and —SO$_3$M where M is an alkali metal cation, for example Na$^+$ or is ammonium, —SO$_3$R$^3$ or CO$_2$R$^3$ where R$^3$ is $C_1$–$C_6$alkyl, phenyl or benzyl, —NH$_2$, $C_1$–$C_8$alkyl or $C_1$–$C_8$dialkylamino, $C_1$–$C_8$acylamino or $C_1$–$C_8$aminocarbonyl. A few examples are methyl, ethyl, n-propyl or isopropyl, n-butyl, i-butyl or t-butyl, methyloxy, ethyloxy, chloroethyloxy, methylthio, chloromethyl, fluoromethyl, trifluoromethyl, trichloromethyl, cyclopentyl, cyclohexyl, acetyl, propionyl, acetyloxy, methoxysulfonyl, methoxycarbonyl or ethoxycarbonyl, methylamino, dimethylamino, acetylamino, aminocarbonyl and dimethylaminocarbonyl.

Examples of nitro compounds are o-, m- and p-chloro or -bromo-nitrobenzene, 2,3-, 3,4-, 2,4-, 2,6-, 3,5- and 2,5-dichloro- or -dibromonitrobenzene, 2,3,4- and 2,3,5-trichloronitrobenzene, 2-chloro-3-bromonitrobenzene, 1-chloro or 1-bromo-2,4-dinitrobenzene, 3,4-dichloro-1,6-dinitrobenzene, 2,4-dichloro-1,6-dinitrobenzene, 1-chloro-2,4,6-trinitrobenzene, 4- or 6-chloro-1-methyl-2-nitrobenzene, 2- or 6-bromo-1-methyl-4-nitrobenzene, 4- or 6-chloro-1-ethyl-2-nitrobenzene, 2- or 3-bromo-1-ethyl-4-nitrobenzene, 4- or 6-chloro-1-methoxy-4-nitrobenzene, 4- or 6-chloro-2-nitrophenol, 1-chloro- or 1-bromo-2-nitronaphthalene, 1-chloro- or 1-bromo-2,7-dinitronaphthalene, 2-chloro-4-nitrodiphenyl, 2,2'-dichloro-4,4'-dinitrodiphenyl, 2-bromo-4,4'-dinitrobenzophenone, bis(3,3'-dichloro-4,4'-dinitrophenyl)methane and 3,3'-dichloro-4,4'-dinitrodiphenyl ether.

The formamidine salt is advantageously used in an amount of 0.1 to 30 mol % preferably 0.1 to 20 mol % and in particular 0.5 to 15 mol %, relative to the nitro compound.

The formamidine cation can be substituted by one, two or three hydrocarbon radicals which contain preferably 1 to 18, particularly 1—12, and especially 1 to 6, carbon atoms. The anion of the formamidine salt can be derived, for example, from aliphatic or aromatic carboxylic acids, preferably mono- or dicarboxylic acids containing preferably 1 to 18, particularly 1–8, and especially 1 to 4, carbon atoms.

A preferred embodiment is that in which the formamidine salt conforms to the formula I

in which R$^1$, R$^2$ and R$^3$, independently of one another, are H, or linear or branched $C_1$–$C_{12}$alkyl, $C_5$cycloalkyl or $C_6$cycloalkyl, $C_6$–$C_{18}$alkylcycloalkyl, $C_6$–$C_{10}$cycloalkylalkyl, $C_7$–$C_{18}$alkylcycloalkylalkyl, where the cycloalkyl contains 5 or 6 ring carbon atoms, $C_6$–$C_{10}$aryl, $C_7$–$C_{18}$alkaryl, $C_7$–$C_{12}$aralkyl or $C_7$–$C_{18}$alkaralkyl or R$^1$ and R$^2$ together are tetramethylene or pentamethylene or 3-oxa-1,5-pentylene, X is the anion of an acid, in particular of a $C_1$–$C_{18}$ mono- or -dicarboxylic acid, and n is 1 or 2.

$R^1$, $R^2$ and $R^3$ as alkyl contain preferably 1 to 6 and in particular 1 to 4 carbon atoms. Examples are methyl, ethyl and the isomers of propyl, butyl, pentyl, hexyl, heptyl, octyl, decyl and dodecyl. $R^1$, $R^2$ and $R^3$ as cycloalkyl are, for example, cyclopentyl and cyclohexyl. $R^1$, $R^2$ and $R^3$ as alkylcycloalkyl preferably contain 6 to 12, in particular 6 to 10, carbon atoms. Examples are methylcyclopentyl, methylcyclohexyl, ethylcyclohexyl and n-propylcyclohexyl. $R^1$, $R^2$ and $R^3$ as cycloalkylalkyl are in particular cyclopentylmethyl or cyclohexylmethyl. $R^1$, $R^2$ and $R^3$ as alkylcycloalkylalkyl contain preferably 7 to 12 carbon atoms and are in particular $C_1$–$C_4$alkylcyclopentylmethyl or $C_1$–$C_4$alkylcyclohexylmethyl. $R^1$, $R^2$ and $R^3$ having the meaning of aryl can be, for example, naphthyl and in particular phenyl. In the aryl-containing radicals for $R^1$, $R^2$ and $R^3$, aryl is in particular phenyl. $R^1$, $R^2$ and $R^3$ having the meaning of alkaryl preferably contain 7 to 12 carbon atoms and are in particular $C_1$–$C_4$alkylphenyl. $R^1$, $R^2$ and $R^3$ as aralkyl are in particular benzyl and phenylethyl. $R^1$, $R^2$ and $R^3$ as alkaralkyl preferably contain 8 to 14 carbon atoms and are in particular $C_1$–$C_4$alkylbenzyl.

$R^1$, $R^2$ and $R^3$ are preferably H or aliphatic or cycloaliphatic radicals.

In a preferred embodiment, $R^1$, $R^2$ and $R^3$, independently of one another, are H or $C_1$–$C_8$alkyl, in particular H, methyl or ethyl and especially they are each H.

In formula I, n is preferably 1.

X as the anion of a mono- or dicarboxylic acid preferably contains 1-18, particularly 1-12 and in particular 1 to 8 carbon atoms. They can be aliphatic or aromatic carboxylic acids which can conform, for example, to the formulae $$R^4COOH \text{ or } R^5(COOH)_2$$

in which $R^4$ is linear or branched alkyl having particularly 1 to 6 carbon atoms or is cyclohexyl, phenyl or benzyl, and $R^5$ is a direct bond, linear or branched $C_2$–$C_6$alkylene or cyclohexylene or phenylene. In particular, X in formula I represents the anion of an aliphatic mono- or dicarboxylic acid having preferably 1 to 4 carbon atoms. Particularly, X represents the anions $(COO)_2{}^{2\ominus}$, $HCOO^\ominus$, $CH_3COO^\ominus$, $CH_3CH_2COO^\ominus$, $CH_3CH_2CH_2COO^\ominus$ or $CH_2(COO)_2{}^{2\ominus}$, and very particularly $CH_3COO^\ominus$.

The formamidine salt is in particular formamidine acetate.

The formamidine salt can be added to the reaction mixture as such or can be generated in situ by a known method before the hydrogenation, for example by hydrogenating a substituted or unsubstituted cyanamide in the presence of Raney nickel and an acid.

The in situ formation of the substituted or unsubstituted formamidine salt takes place at such a high rate that this reaction can be carried out in the presence of a halogenated aromatic nitro compound. In this reaction, some of the nitro compound can be added and the remainder can be metered in, or the total amount of nitro compound can be introduced initially as well.

The amount of Raney nickel is preferably 0.5 to 20% by weight, particularly 1 to 10% by weight, relative to the nitro compound.

The hydrogenation is carried out without solvent or in an inert solvent. Examples of suitable solvents are alkanols (methanol, ethanol, propanol, butanol, methoxyethanol or ethoxyethanol), ethers (dibutyl ether, t-butyl methyl ether, tetrahydrofuran, dioxane, ethylene glycol dimethyl ether, diethylene glycol dimethyl ether), amides and lactams (dimethylformamide, dimethylacetamide, N-methylpyrrolidone), esters and lactones (ethyl acetate, γ-butyrolactone), hydrocarbons (pentane, hexane, methylcyclohexane, benzene, toluene, xylene, chlorobenzene), and water. In the hydrogenation without solvent, the halogenated aromatic amine resulting in the hydrogenation is the solvent.

In a preferred embodiment, the solvent used is a $C_1$–$C_4$alkanol by itself or in a mixture with water. In particular, methanol is used.

The reaction temperature is advantageously 50° to 120° C. The pressure is preferably 1 to 30 bar. The reaction time depends mainly on the reaction conditions and is in general less than two hours.

The process according to the invention can be carried out in such a manner that the nitro compound, the Raney nickel, the solvent and the formamidine salt is introduced into an autoclave and the air is first displaced by nitrogen which is then displaced by hydrogen. The autoclave is then sealed, hydrogen is injected until the desired pressure is reached, and the mixture is heated to the reaction temperature. After the reaction is completed, the reaction mixture is separated off from the catalyst. The reaction product can then be freed from the water of reaction and solvent and be further purified by distillation or recrystallization. As is known, the primary aromatic amines are intermediates for the preparation of dyes.

The examples which follow illustrate the invention in more detail.

EXAMPLE 1

40.8 g of 1-chloro-2,4-dinitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 10 bar and a temperature of 60° C. The hydrogenation time is 1¼ hours. 1-Chloro-2,4-diaminobenzene, 99% pure (analysed as 1-Chloro-2,4-acetamidobenzene by liquid chromatography), is obtained in quantitative yield.

EXAMPLE 2

39.8 g of 1-chloro-2-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 10 bar and a temperature of 90° C. The hydrogenation time is 1½hours. 1-Chloro-2-aminobenzene, 99.4% pure (analysed by gas chromatography), is obtained in quantitative yield.

EXAMPLE 3

39.8 g of 1-chloro4-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 12 bar and a temperature of 80° C. The hydrogenation time is 1½ hours. 1-Chloro-4-aminobenzene, 99.7% pure (analysed by gas chromatography), is obtained in quantitative yield.

EXAMPLE 4

39.8 g of 1-chloro-3-nitrobenzene, 2 g of Raney nickel (60%, aqueous), 1.5 g of formamidine acetate and 120 ml of methanol are introduced in an autoclave equipped with gas introduction stirrer. The air is then displaced by nitrogen and then by hydrogen. The hydrogenation is carried out at a pressure of 12 bar and a temperature of 80° C. The hydrogenation time is 1½ hours. 1-Chloro-3-aminobenzene, 99.4% pure (analysed by gas chromatography), is obtained in quantitative yield.

EXAMPLE 5

48.0 g of 1,2-dichloro-4-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 12 bar and a temperature of 80° C. The hydrogenation time is 1 hour. 1,2-Dichloro-4-aminobenzene, 99.7% pure (analysed by gas chromatography), is obtained in quantitative yield.

EXAMPLE 6

48.0 g of 1,4-dichloro-2-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 12 bar and a temperature of 80° C. The hydrogenation time is 1 hour. 1,4-Dichloro-2-aminobenzene, 99.6% pure (analysed by gas chromatography), is obtained in quantitative yield.

EXAMPLE 7

48.0 g of 1,2-dichloro-3-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 12 bar and a temperature of 80° C. The hydrogenation time is 1 hour. 1,2-Dichloro-3-aminobenzene, 99.7% pure (analysed by gas chromatography), is obtained in quantitative yield.

EXAMPLE 8

50.5 g of 1-bromo-2-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 10 bar and a temperature of 65° C. The hydrogenation time is 2½ hours. 1-Bromo-2-aminobenzene, 97.8% pure (analysed by gas chromatography), is obtained in quantitative yield.

EXAMPLE 9

50.5 g of 1-bromo-3-nitrobenzene, 2 g of Raney nickel (60%, aqueous), 1.5 g of formamidine acetate and 120 ml of methanol are introduced in an autoclave equipped with gas introduction stirrer. The air in the autoclave is then displaced by nitrogen and then by hydrogen. The hydrogenation is carried out at a pressure of 10 bar and a temperature of 65° C. The hydrogenation time is 2 hours. 1-Bromo-3-aminobenzene, 98.7% pure (analysed by gas chromatography), is obtained in quantitative yield.

EXAMPLE 10

40.8 g of 1-chloro-2,4-dinitrobenzene, 2 g of Raney nickel (60%, aqueous), 2.3 g of N,N'-dibutylformamidine acetate and 120 ml of methanol are introduced in an autoclave equipped with gas introduction stirrer. The air in the autoclave is then displaced by nitrogen and then by hydrogen. The hydrogenation is carried out at a pressure of 10 bar and a temperature of 60° C. The hydrogenation time is 1¼ hours. 1-Chloro-2,4-diaminobenzene, 97% pure (analysed as 1-Chloro-2,4-acetamidobenzene by liquid chromatography), is obtained in quantitative yield.

EXAMPLE 11

39.8 g of 1-chloro-2-nitrobenzene, 2 g of Raney nickel (60%, aqueous), 1.5 g of formamidine acetate, 100 ml of toluene and 20 ml of methanol are introduced in an autoclave equipped with gas introduction stirrer. The air in the autoclave is then displaced by nitrogen and then by hydrogen. The hydrogenation is carried out at a pressure of 10 bar and a temperature of 90° C. The hydrogenation time is 4 hours. 1-Chloro-2-aminobenzene, 99.9% pure (analysed by gas chromatography), is obtained in quantitative yield.

EXAMPLE 12

1.5 g of cyanamide, 1.5 g of acetic acid, 2 g of Raney nickel (60%, aqueous), and 120 ml of methanol are introduced in an autoclave equipped with gas introduction stirrer. Under a hydrogen pressure of 4 bar and a temperature of 25° C., the cyanamide is hydrogenated quantitatively to the formamidine acetate. 40.8 g of 1-chloro-2,4-dinitrobenzene are then added to the autoclave, and the hydrogenation is carried out at a pressure of 10 bar and a temperature of 60° C. The hydrogenation time is 1 hour. 1-Chloro-2,4-diaminobenzene, 97.5% pure (analysed as 1-Chloro-2,4-acetamidobenzene by liquid chromatography), is obtained in quantitative yield.

EXAMPLE 13

3 g of dicyanodiamide, 3 g of acetic acid, 2 g of Raney nickel (60%, aqueous), and 120 ml of methanol are introduced in an autoclave equipped with gas introduction stirrer. Under a hydrogen pressure of 4 bar and a temperature of 25° C., the dicyanodiamide is hydrogenated to the formamidine acetate. 40.8 g of 1-chloro-2,4-dinitrobenzene are then added to the autoclave, and the hydrogenation is carried out at a pressure of 10 bar and a temperature of 60° C. The hydrogenation time is 1¼ hours. 1-Chloro-2,4-diaminobenzene, 98% pure (analysed as 1-Chloro-2,4-acetamidobenzene by liquid chromatography), is obtained in quantitative yield.

What is claimed is:

1. A process for the preparation of halogenated aromatic primary amines by catalytic hydrogenation of halogenated aromatic nitro compounds in the presence of Raney nickel at a pressure of 0.1 to 100 bar and at a temperature of 30° to 150° C. in an inert solvent and in the presence of an inhibitor against dehalogenation, wherein the inhibitor is a formamidine salt.

2. A process according to claim 1, wherein the formamidine salt is used in an amount of 0.1 to 30 mol %, relative to the nitro compound.

3. A process according to claim 2, wherein the formamidine salt is used in an amount of 0.5 to 15 mol %.

4. A process according to claim 1, wherein the formamidine salt conforms to the formula I

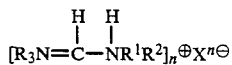
(I)

in which $R^1$, $R^2$ and $R^3$, independently of one another, are H, or linear or branched $C_1$–$C_{12}$alkyl, $C_5$cycloalkyl or $C_6$cycloalkyl, $C_6$–$C_{18}$alkylcycloalkyl, $C_6C_{10}$cycloalkylalkyl, $C_7$–$C_{18}$alkylcycloalkylalkyl, where the cycloalkyl contains 5 or 6 ring carbon atoms, $C_6$–$C_{10}$aryl, $C_7$–$C_{18}$alkaryl, $C_7$–$C_{12}$aralkyl or $C_7$–$C_{18}$alkaralkyl or $R^1$ and $R^2$ together are tetramethylene or pentamethylene or 3-oxa-1,5-pentylene, X is the anion of an acid, in particular of a $C_1$–$C_{18}$ mono- or -dicarboxylic acid, and n is 1 or 2.

5. A process according to claim 4, wherein $R^1$, $R^2$ and $R^3$, independently of one another, are H, or an aliphatic or cycloaliphatic group.

6. A process according to claim 4, wherein in formula I $R^1$, $R^2$ and $R^3$, independently of one another, are H or $C_1$–$C_6$alkyl.

7. A process according to claim 4, wherein in formula I $R^1$, $R^2$ and $R^3$, independently of one another, are H, methyl or ethyl.

8. A process according to claim 4, wherein in formula I $R^1$, $R^2$ and $R^3$, independently of one another, are each H.

9. A process according to claim 4, wherein n in formula I is 1.

10. A process according to claim 4, wherein X in formula I as the anion of a carboxylic acid contains 1 to 8 carbon atoms.

11. A process according to claim 4, wherein X in formula I is the anion of an aliphatic $C_1$–$C_4$ mono- or -dicarboxylic acid.

12. A process according to claim 11, wherein X in formula I is $(COO)_2^{2\ominus}$, $HCOO^\ominus$, $CH_3COO^\ominus$, $CH_3CH_2COO^\ominus$, $CH_3CH_2CH_2COO^\ominus$ or $CH_2(COO)_2^{2\ominus}$.

13. A process according to claim 11, wherein X is $CH_3COO^-$.

14. A process according to claim 1, wherein the formamidine salt is formamidine acetate.

15. A process according to claim 1, wherein the Raney nickel is used in an amount of 0.5 to 20% by weight, relative to the nitro compound.

16. A process according to claim 1, wherein the solvent used is a $C_1$–$C_4$alkanol by itself or in a mixture with water.

17. A process according to claim 16, wherein the solvent is methanol.

18. A process according to claim 1, wherein the temperature is 50° to 120° C.

19. A process according to claim 1, wherein the pressure is 1 to 30 bar.

20. A process according to claim 1, wherein the formamidine salt is prepared by hydrogenation of corresponding cyanamide in the presence of an acid in situ and the halogenated aromatic nitro compound is either initially introduced as well in its total amount or partially introduced as well and the remainder is metered in later.

* * * * *